United States Patent
Dicarlo et al.

(10) Patent No.: US 12,053,304 B2
(45) Date of Patent: Aug. 6, 2024

(54) BIOSENSOR CAPSULE AND SYSTEM

(71) Applicant: ENTERASENSE LIMITED, Galway (IE)

(72) Inventors: Maria Chiara Dicarlo, Galway (IE); Donal Devery, Galway (IE)

(73) Assignee: Enterasense Limited, Galway (IE)

( * ) Notice: Subject to any disclaimer, the term of this patent is extended or adjusted under 35 U.S.C. 154(b) by 425 days.

(21) Appl. No.: 17/603,296

(22) PCT Filed: Apr. 16, 2020

(86) PCT No.: PCT/EP2020/060788
§ 371 (c)(1),
(2) Date: Oct. 12, 2021

(87) PCT Pub. No.: WO2020/212538
PCT Pub. Date: Oct. 22, 2020

(65) Prior Publication Data
US 2022/0183629 A1    Jun. 16, 2022

(30) Foreign Application Priority Data

Apr. 18, 2019 (EP) ..................... 19170030

(51) Int. Cl.
*A61B 5/00* (2006.01)
*A61B 5/07* (2006.01)
*A61B 5/1459* (2006.01)

(52) U.S. Cl.
CPC .......... *A61B 5/6861* (2013.01); *A61B 5/0071* (2013.01); *A61B 5/073* (2013.01); *A61B 5/1459* (2013.01); *A61B 5/7225* (2013.01)

(58) Field of Classification Search
CPC ..... A61B 5/6861; A61B 5/0071; A61B 5/073; A61B 5/1459; A61B 5/7225; A61B 5/145
See application file for complete search history.

(56) References Cited

U.S. PATENT DOCUMENTS 7,828,730 B2   11/2010   Schostek et al.
2013/0053928 A1   2/2013   Gat et al.
(Continued)

FOREIGN PATENT DOCUMENTS

CN   104271028 A   1/2015
CN   105919646 A   9/2016
(Continued)

OTHER PUBLICATIONS

An Extended European Search Report issued by the European Patent Office on Dec. 14, 2023, which corresponds to EP Patent Application No. 23201010.8, which is a divisional of EP Patent Application No. 22188611.2, and is related to U.S. Appl. No. 17/603,296.
(Continued)

*Primary Examiner* — Eric F Winakur
*Assistant Examiner* — Abid A Mustansir
(74) *Attorney, Agent, or Firm* — Studebaker & Brackett PC

(57) ABSTRACT

A biosensor system has a capsule with a housing configured for ingesting in a mammal GI tract, being cylindrical with domed ends. The housing forms an external space akin to a "cut-out" shape with two opposing transparent walls facing each other in the longitudinal direction and a base wall facing radially. An LED emitter emits at a number of wavelengths in time sequence, and radiation is detected by a photo-detector via the wall which forms a concave lens. An antenna is for wireless transmission of data to an external device and is in the form of conical spiral in an overall conical shape, located for optimum space efficiency in a domed end. A battery compartment is at the opposed end of the housing, separated from the antenna by the external space.

13 Claims, 14 Drawing Sheets

(56) References Cited

U.S. PATENT DOCUMENTS

| | | | |
|---|---|---|---|
| 2014/0275860 A1 | 9/2014 | Rottenberg et al. | |
| 2014/0296666 A1* | 10/2014 | Rabinovitz | A61B 1/063 |
| | | | 600/310 |
| 2018/0064871 A1 | 3/2018 | James | |
| 2020/0229687 A1* | 7/2020 | Schurr | A61B 5/02042 |

FOREIGN PATENT DOCUMENTS

| | | |
|---|---|---|
| EP | 0160768 A1 | 11/1985 |
| EP | 2057934 A1 | 5/2009 |
| EP | 3269298 A1 | 1/2018 |
| JP | 60-236631 A | 11/1985 |
| JP | H08-193946 A | 7/1996 |
| JP | 2005-192879 A | 7/2005 |
| JP | 2009-233253 A | 10/2009 |
| JP | 2011-513865 A | 4/2011 |
| JP | 2014-505556 A | 3/2014 |
| JP | 2015-512664 A | 4/2015 |
| JP | 2015-226790 A | 12/2015 |
| JP | 2017-525440 A | 9/2017 |
| WO | 2005/113374 A2 | 12/2005 |
| WO | 2009/111664 A2 | 9/2009 |
| WO | 2011016002 A1 | 2/2011 |
| WO | 2011/066431 A2 | 6/2011 |
| WO | 2012107717 A1 | 8/2012 |
| WO | 2013/088444 A2 | 6/2013 |
| WO | 2013121276 A1 | 8/2013 |
| WO | 2016015999 A1 | 2/2016 |
| WO | 2018/112389 A1 | 6/2018 |

OTHER PUBLICATIONS

International Search Report issued in PCT/EP2020/060788; mailed Aug. 3, 2020.

The Extended European Search Report issued by the European Patent Office on Jan. 20, 2023, which corresponds to EP 22188611.2-1113 and is related to U.S. Appl. No. 17/603,296.

An Office Action issued by the Japanese Patent Office on Dec. 12, 2023, which corresponds to Japanese Patent Application No. 2021-562105 and is related to U.S. Appl. No. 17/603,296.

An Office Action issued by the Chinese Intellectual Property Office on Jan. 6, 2024, which corresponds to Chinese Patent Application No. 202080029471.9 and is related to U.S. Appl. No. 17/603,296.

An Office Action issued by the Chinese Intellectual Property Office on May 10, 2024, which corresponds to Chinese Patent Application No. 17/603,296.9 and is related to U.S. Appl. No. 17/603,296. (CN 104271028 A was previously cited on Feb. 20, 2024.).

* cited by examiner

"CURRENT LED PATTERN"

BIOSENSOR CAPSULE AND SYSTEM

INTRODUCTION

The invention relates to a wireless biosensor in the form of a capsule to monitor the presence of blood or other fluids within the gastrointestinal (GI) tract, and to a system incorporating the biosensor.

U.S. Pat. No. 7,828,730B2 describes a device for haemorrhage detection, comprising a fixing means mountable inside a hollow organ, and a detecting means connected to the fixing means for detecting presence of blood, and measuring specific absorption spectra of content in the hollow organ. This requires a sensor to be fixed within at least one organ.

It is known to use fluorescein as a marker for active bleeding detections. WO2011066431 describes a system and method for wireless biosensor using fluorescein as the marker.

EP3269298 (Ovesco Endoscopy) describes a capsule with a recess and a shielding plate to prohibit emitted light from bypassing the recess.

WO2018/112389 (Progenity) describes an ingestible device with a detection chamber (22) formed by a depression.

US2014/0296666 (Given Imaging) describes an in-vivo sensing device with a plurality of illumination sources on a first side of a gap, each for repeatedly irradiating the fluids within the with the gap at a different narrow band wavelength, for determining a series of blood concentration values. A bleeding event is determined based on a series of blood concentration values as a function of time, and a threshold.

US2014/275860 (Given Imaging Ltd) describes a device with a housing that includes a gap, an illumination source for illuminating the in-vivo fluids in the gap, a light detector for detecting light which passes through the in-vivo fluids in the gap, and flexible on the housing in the vicinity of the gap's opening for covering the opening when the fins are folded.

WO2005/113374 (Given Imaging Ltd) describes a device, system and method for in-vivo sampling, with a sampling chamber and a gating mechanism, in which a sampling chamber may store a sample of a body lumen substance, and the gate may close and open an opening of the sampling chamber.

US2013/0053928 (Daniel Gat) describes a capsule with a transparent case and one or more radiation sources to treat detected pathological lesions inside the gastrointestinal (GI) tract with light during the passage of the device through the GI tract.

The invention is directed towards providing an improved wireless biosensor monitor.

SUMMARY OF THE INVENTION

We describe a biosensor system in various embodiment as set out in the accompanying claims 1 to 47.

We describe a biosensor system comprising:
a capsule comprising:
  a housing configured for ingesting in a mammal GI tract and having a longitudinal axis, at least some portions of the housing being transparent to radiation of a sensing wavelength, and wherein the housing is configured to form an external space which is open to access by fluids,
  a radiation emitter and a radiation detector arranged to emit radiation into said external space and to detect radiation from said external space, through said transparent portions of the housing,
  a drive circuit for the radiation emitter and a signal processing circuit linked to the detector, and
  an interface with an antenna for wireless transmission of data to an external device and/or a processor for locally processing and storing detection data.

Preferably, the external space is formed by a plurality of walls forming an open space within an envelope of the housing. Preferably, the housing comprises a base wall facing in a direction having a primarily radial component, and first and second walls substantially facing each other in the longitudinal direction, said walls forming said external space. Preferably, at least one of said walls is planar, and preferably all of said walls are planar.

Preferably, the first and second walls are for passage of radiation in the longitudinal direction for absorption detection of material within the external space. Preferably, the base wall is for detection of fluorescence light emitted in the radial direction within the external space. Preferably, the housing forms a convex lens for passage of radiation from the emitter into the external space, and a concave lens for passage of radiation into the detector.

Preferably, the housing forms said external space with a dimension in the longitudinal direction in the range of 2 mm to 7 mm Preferably, the first and second walls are splayed radially outwardly relative to each other. Preferably, the length of the housing in the longitudinal direction is in the range of 15 mm to 30 mm, and its maximum width dimension is in the range of 5 mm to 12 mm.

Preferably, the housing envelope shape is substantially cylindrical with domed ends. Preferably, the housing comprises a plurality of parts which are joined together, and a part which forms said external space is transparent to said radiation.

Preferably, the housing comprises a fluorescence detector arranged to detect fluorescence through a transparent part of the housing, and said detection may be simultaneously with absorption detection or separately from absorption detection.

Preferably, the signal processing circuit comprises a processor mounted on a controller circuit board which extends in a longitudinal direction and overlaps with said external space. Preferably, the wireless interface includes an antenna which is mounted in a domed end of the housing. Preferably, the antenna is in the form of a spiral with decreasing diameter in a direction towards an end of the housing.

Preferably, the antenna has a maximum radial dimension in the range of 7.5 mm to 9 mm and it narrows to form an apex with a radial dimension in the range of 2 mm to 4 mm Preferably, the number of turns of the antenna is in the range of 7 to 10. Preferably, the antenna shape outer envelope substantially forms an angle to the longitudinal axis in the range of 60° to 80°.

Preferably, the wireless interface comprises RF circuits located physically adjacent the antenna, on a board extending longitudinally.

Preferably, the signal processing circuit comprises a processor mounted on a circuit board extending longitudinally. Preferably, the capsule comprises a power management circuit board mounted transversely across the housing and defining a space for a battery compartment. Preferably, the battery compartment is also bounded by a circuit board for the radiation emitter.

Preferably, the radiation emitter comprises one or more LEDs and the detector comprises one or more photodetectors. Preferably, the signal processing circuit is configured to take a plurality of readings for a particular radiation wavelength and to eliminate outliers and to average non-outlier readings.

Preferably, the emitter comprises a plurality of emitter devices each adapted to emit at a particular wavelength and the drive circuit is configured to activate each emitter device according to a time multiplex scheme. Preferably, the time separation between activations is in the range of 2 ms to 5 ms.

Preferably, the signal processing circuit is configured to take a radiation reading when the emitter is inactive and to use said reading as base or control to eliminate background noise.

Preferably, the signal processing circuit is configured to determine an indication of presence of a particular fluid according to a ratio of detected signal for one emitter wavelength to that of another emitter wavelength. Preferably, there is a particular ratio threshold for each of a plurality of combinations of radiation wavelengths.

Preferably, said combinations include one or more of: red:green, far red:green, red:blue, far red:blue, far red:red. Preferably, the signal processing circuit is configured to determine an indication of presence of a particular fluid according to determining an angle as an arctan of a wavelength difference divided by a difference in detected signal, and comparing said determined angle with a threshold angle.

Preferably, the signal processing circuit is configured to determine a severity value for an indication of presence of a particular fluid according to detected signal amplitude for one or more radiation wavelengths. Preferably, said severity value is an indicator of extent of internal bleeding.

Preferably, the signal processing circuit is configured to determine a proportion of fall in detected signal strength for one or more emitter wavelengths as a parameter in determining the severity value. Preferably, the signal processing circuit (50) is configured to monitor change of a detected signal value as an indicator of extent of internal GI tract bleeding Preferably, the signal processing circuit is configured to determine that if the severity index is rising it indicates that fresh blood is present and not historical or previous bleeding.

Preferably, the biosensor system further comprises a receiver for receiving and processing radiation signals emitted by the capsule. Preferably, said receiver includes some of said signal processing circuit.

BRIEF DESCRIPTION OF THE DRAWINGS

The invention will be more clearly understood from the following description of some embodiments thereof, given by way of example only with reference to the accompanying drawings in which.

DESCRIPTION OF THE EMBODIMENTS

Figure 1:
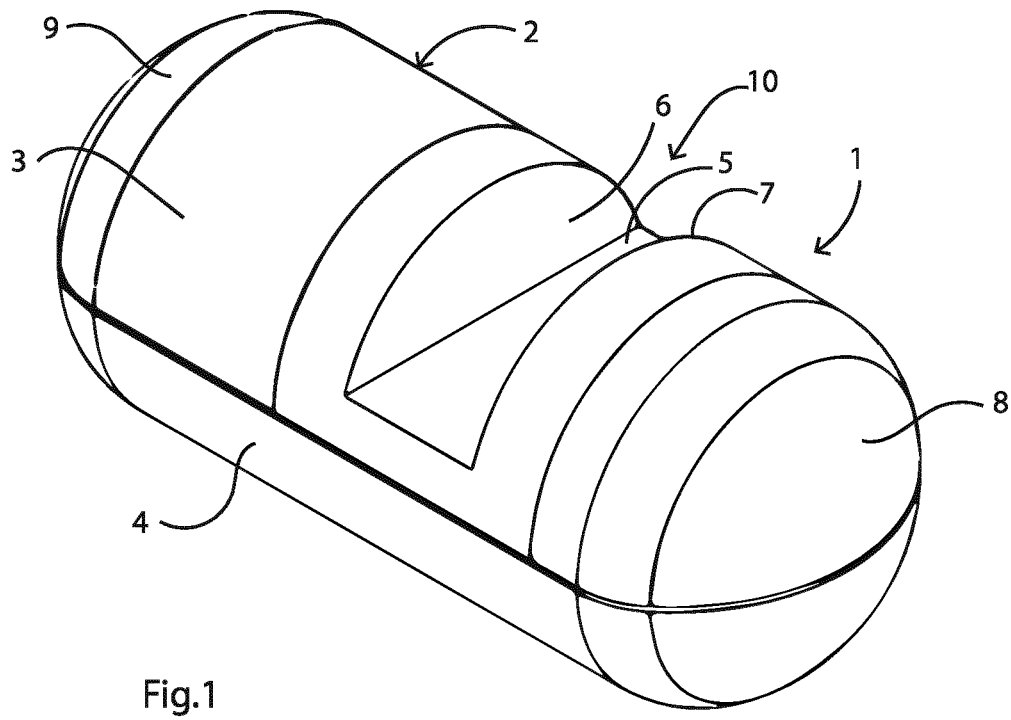
FIGS. 1 and 2 are perspective views.
Figure 2:
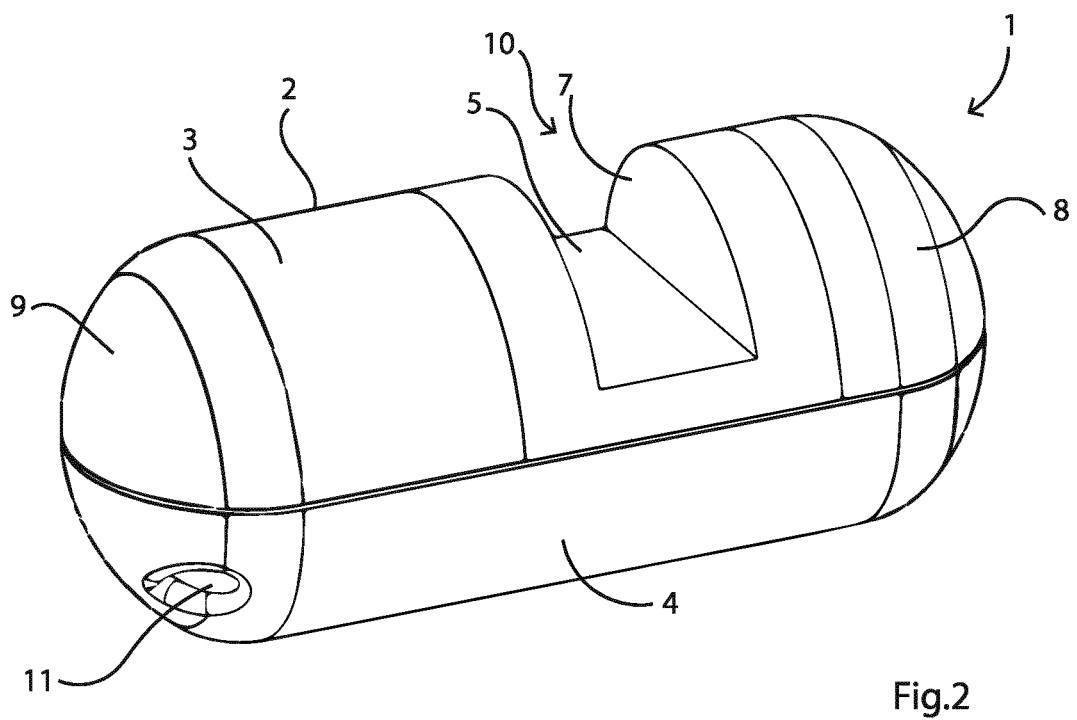
Figure 3:
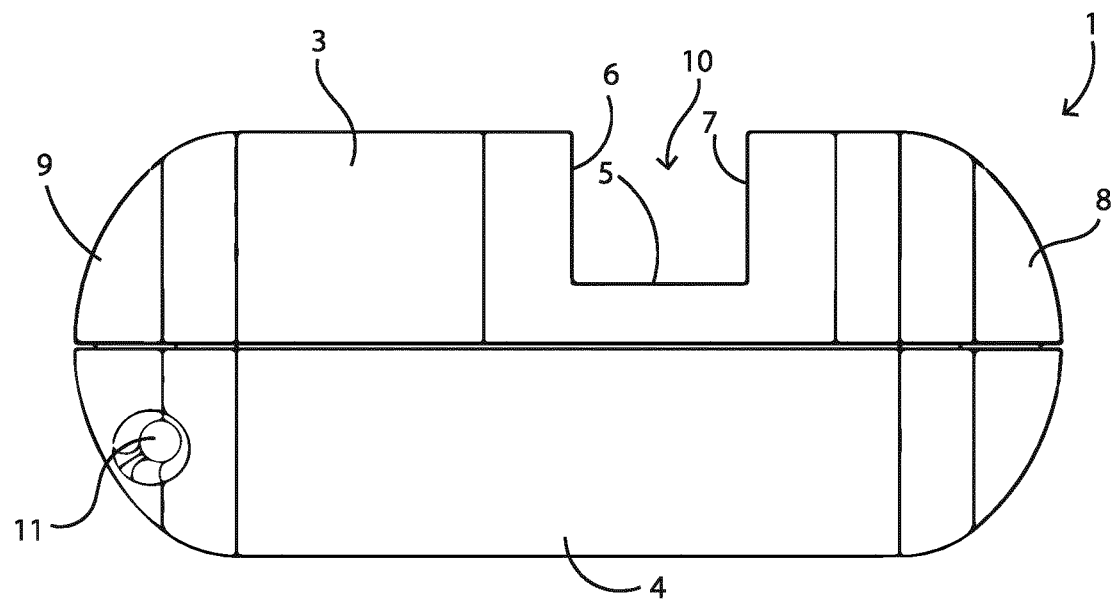
FIG. 3 is a side view, of a biosensor capsule of a sensing system.
Figure 4:
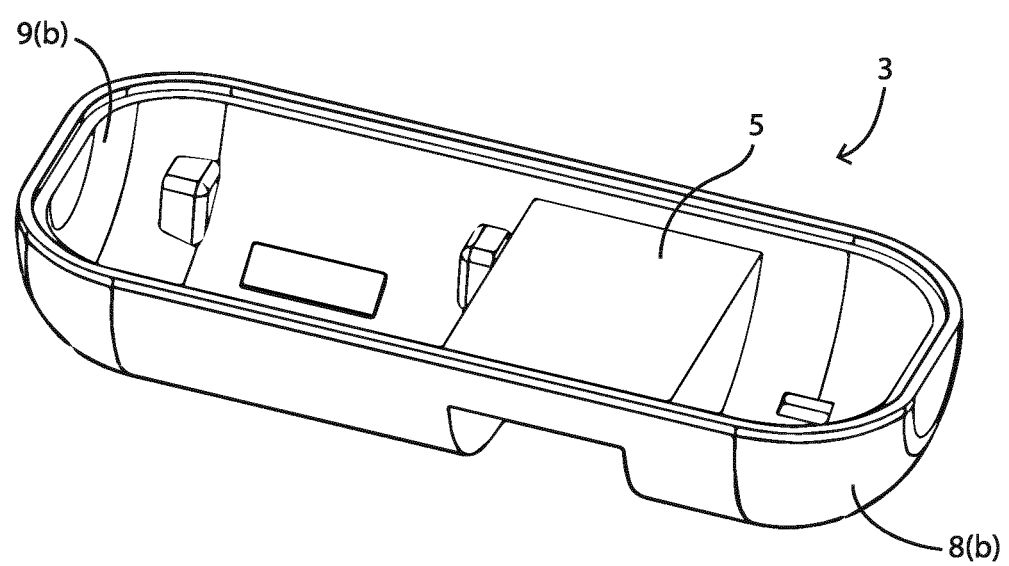
FIG. 4 is an underneath perspective view of a top housing part.
Figure 5A:
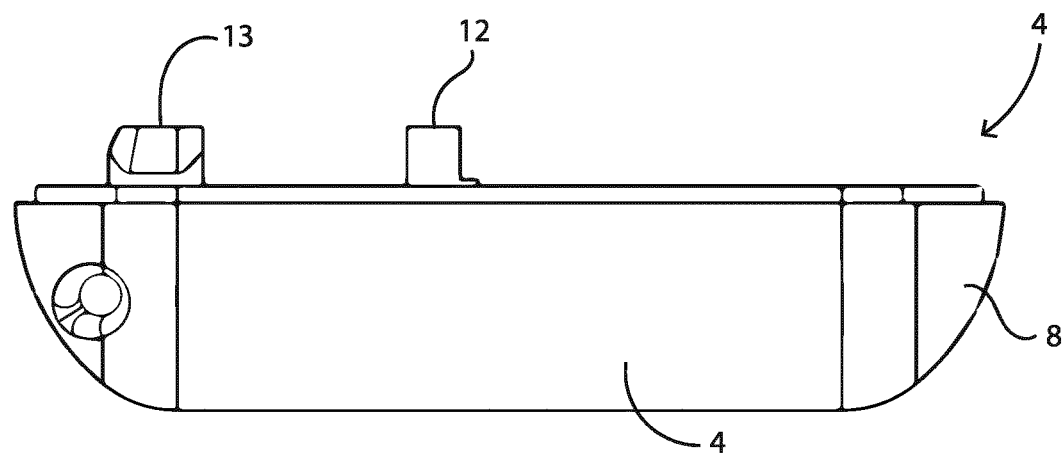
FIGS. 5(a) and 5(b) are side and perspective views of a bottom housing part.
Figure 5B:
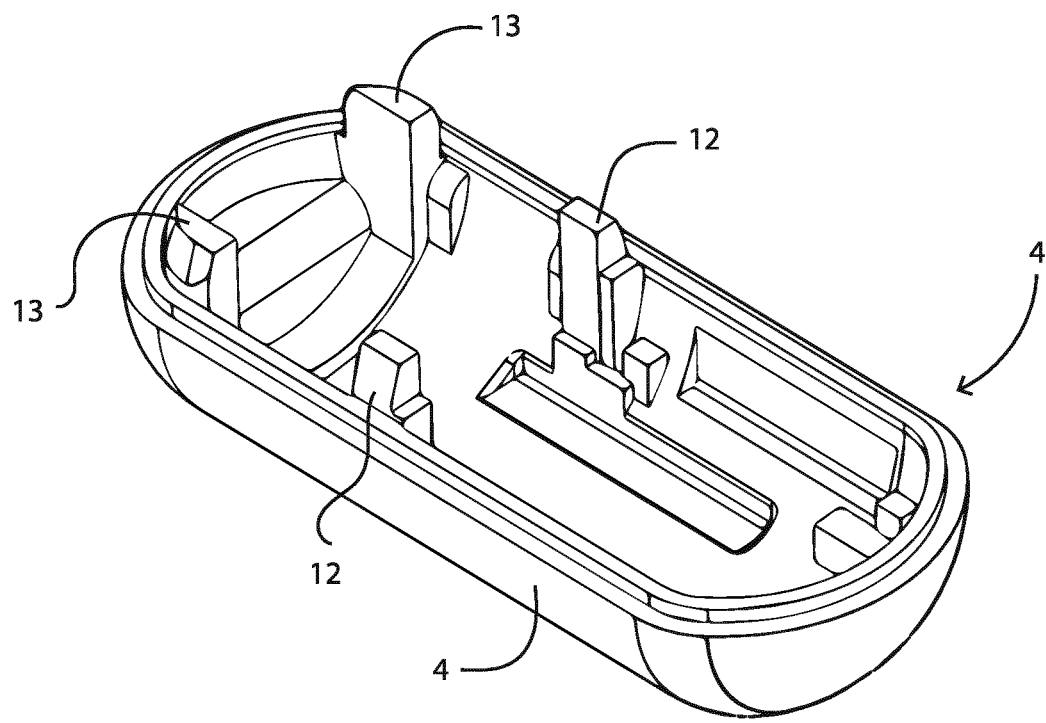

Referring initially to FIGS. 1 to 5 a biosensor capsule 1 of a sensing system is described. The biosensor capsule 1 is configured to be ingested and to measure and monitor the presence of blood or other fluids within the gastrointestinal (GI) tract. The capsule 1 is also configured to enable data collection and wireless transmission to a receiver 70 (FIG. 10) which also forms part of the sensing system. Data can be viewed in real time and/or stored within an external monitor and/or within a cloud-based system for further review and analysis though a user-friendly interface.

The biosensor capsule 1 is configured to identify blood within the GI tract of the patient. This includes blood that may be accumulated in the stomach of a patient for few hours, and is not actively bleeding at the time of ingestion ("old blood"). The capsule also identifies the presence of on-going active bleeding, i.e. blood accumulated in the stomach at the time of ingestion. The capsule is configured to distinguish between "old blood" and "active bleeding".

As shown in FIGS. 1 to 5, the capsule 1 comprises a housing or enclosure 2 which comprises a top portion 3 and a base portion 4. The enclosure 2 has a generally cylindrical shape with first and second domed ends 8 and 9, and an external space "cut-out" volume formed by an indentation 10 in the housing 2 between the domed ends 8 and 9. The cut-out 10 forms a volume within the overall envelope of the capsule 1, and is formed by three planar walls, 5, 6, and 7 of the top portion 3. The wall 6 is transparent to the sensing wavelengths of interest and faces in the longitudinal direction towards the opposing transparent wall 7, and a base of the cut-out is formed by the wall 5. As described in more detail below, the lens walls 6 and 7 are for passage of light in the longitudinal direction for absorption detection of material within the cut-out volume. As described in more detail below, referring to FIG. 15, in other embodiments the components of the capsule may be arranged for fluorescein detection in addition to light absorption.

While the "cut out" volume in this example has walls 5, 6, and 7 which are orthogonal they may be arranged with mutual angles as follows for optimising optical performance.

The materials and geometry of the capsule have been selected to increase the flow of the gastric liquids toward the notch of the capsule and reduce the risk of obstruction from food and other particles. The manner in which the components are mounted within the enclosure is very important in order to minimize volume.

The base portion 4 and the top portion 3 are releasably attached, and the base 4 comprises snap-fitting features 12 and 13. The dimensions of the capsule are:
Length: 27 mm, preferably in the range of 15 mm to 30 mm.
Diameter: 11 mm, preferably in the range of 5 mm to 12 mm.

The lens walls 6 and 7 can be manufactured as one piece and act as the overall top portion 3 of the capsule 1 as in this example. In alternative arrangements it may be assembled as a cut-out component with the top of the capsule. Or, alternatively, different lenses may be manufactured to individually provide each wall assembled with the top capsule.

The wall 6 comprises a convex lens to diffuse as much light as possible while the walls 5 and 7 are made from a concave lens to focus as much light as possible. As will be described with reference to FIG. 15 the wall 5 may be used as a transparent lens for receiving radiation, such as fluorescent radiation.

The distance between the walls 6 and 7 is 4.5 mm, and more generally is preferably in the range of 2 mm to 7 mm. The transparent walls facing each other may in various embodiments have an angle with respect to the longitudinal axis ranging from 90° to 150°, and in this embodiment the walls 6 and 7 are at 90°+draft angle, to facilitate content to be analysed.

The transparent walls are, in various embodiments, of polycarbonate, PMMA, Polyethylene Terephthalate (PET), Amorphous Copolyester (PETG), Polyvinyl Chloride (PVC), Liquid Silicone Rubber (LSR), Cyclic Olefin Copolymers, Polyethylene (PE), Transparent Polypropylene (PP), Styrene Methyl Methacrylate (SMMA), Polystyrene, MABS (Transparent ABS).

In this embodiment there is one "cut-out" (pair of opposing transparent walls). However, in other embodiments there may be a second cut-out section on the opposite side of the capsule.

Figure 6:
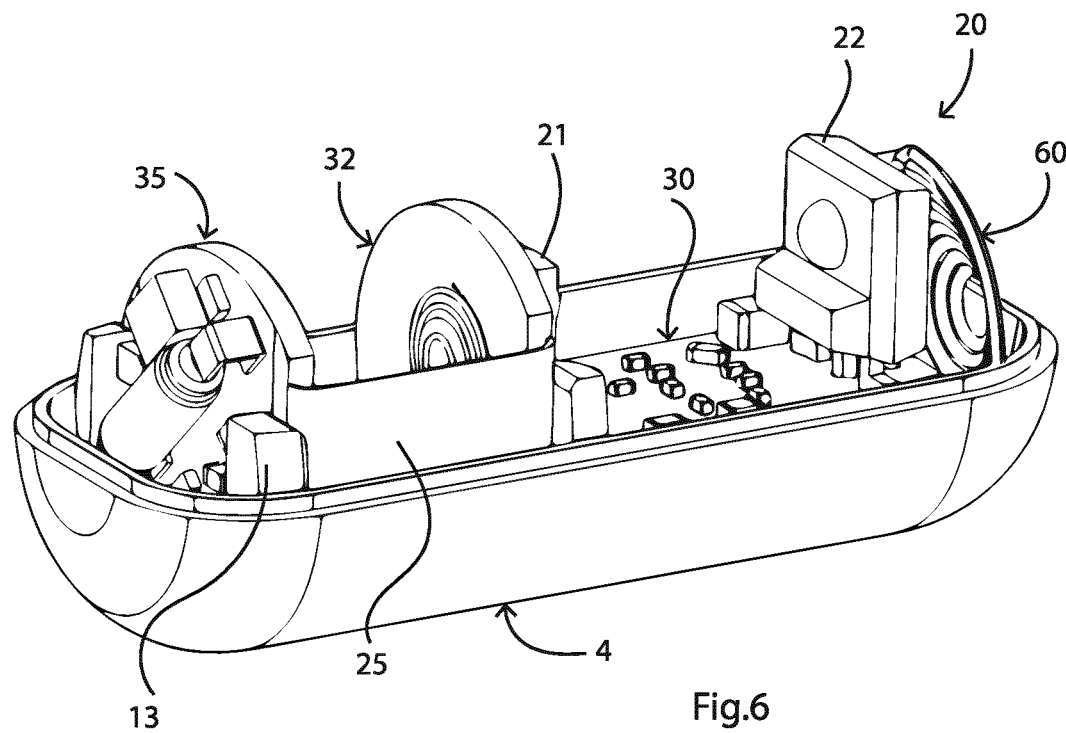
FIG. 6 is a perspective view of the capsule with the top housing part removed.
Figure 7A:
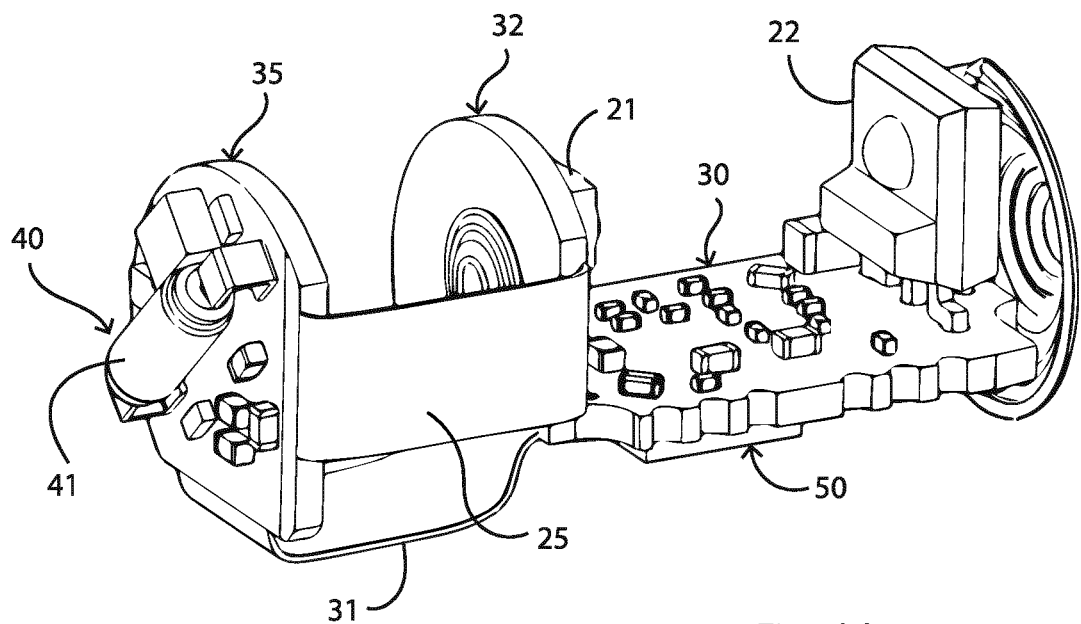
FIGS. 7(a) and 7(b) are top and underneath perspective views respectively of the internal components of the sensor.
Figure 7B:
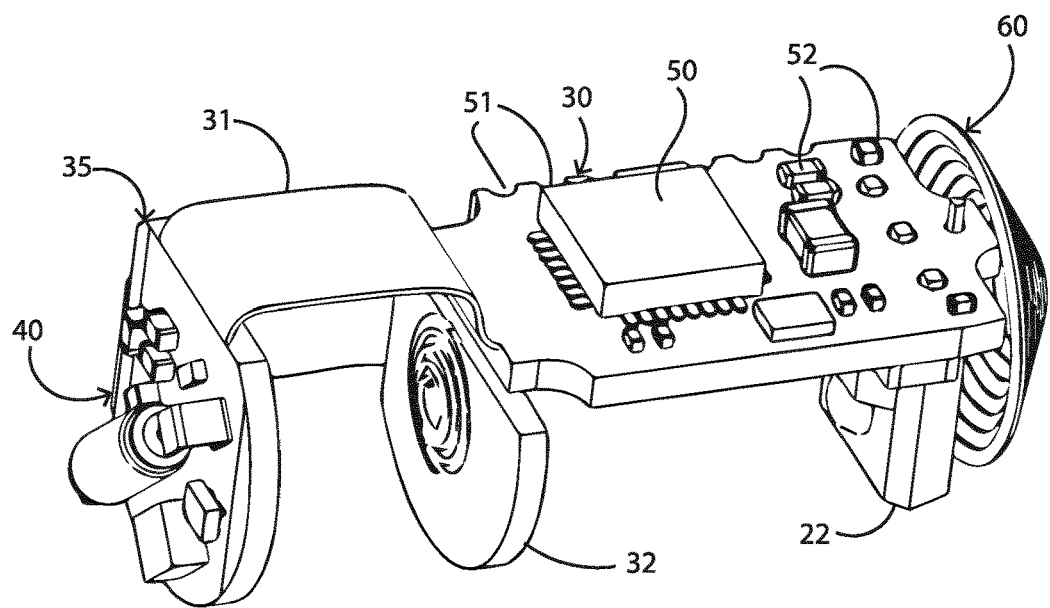
Figure 8:
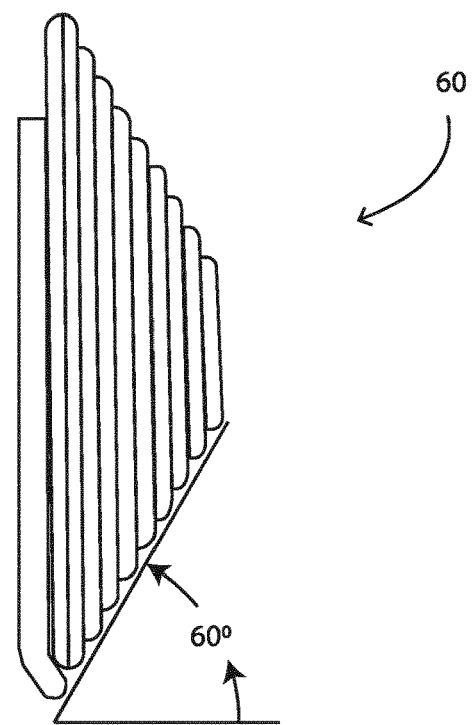
FIG. 8 is a side view of an antenna of the capsule.

An assembly 20 of components of the capsule 1 is shown in FIGS. 6 to 8. The assembly 20 comprises an LED light source 21 aligned in the longitudinal direction with an absorption photodetector 22. Several of the components are mounted on a controller circuit board 30 extending in the longitudinal direction substantially parallel to the base wall 5. This is linked by a flexible cable 31 to an orthogonal emitter circuit board 32 which supports the light source 21 and associated components. There is also a power supply circuit board 35 with components including a magnetic switch, a boost and associated components spaced apart from the emitter circuit board 32, defining a space between for batteries 45. The board 32 is linked to the board 35 by a semi-flex PCB 25 which is retained between the fasteners 12 and 13.

As is clear from FIGS. 6 and 7 the arrangement of the controller board being longitudinal and the emitter and power boards 32 and 35 being transverse and orthogonal allows optimum fitting of components, including the relatively large microcontroller 50 in the space beneath the cut-out space base wall 5. Optimum use is made of the space distal of the cut out 5-7 to accommodate the batteries and associated power components. This helps to ensure that the capsule is not excessively large, while having enough power for a sensing duration greater than 3 days.

The microcontroller 50 being mounted underneath the board 30 allows optimum use of the space between the board and the housing wall. Also, the board 50 has notches on one side for test probe access to pins of the microcontroller 50 and ensure programming of the microcontroller 50.

The antenna 60 is in a spiral shape with decreasing diameter to form a conical shape with an apex towards the end 8 of the housing. In the optimum configuration the antenna has nine full circular turns, the largest of which has diameter of 8.6 mm. The antenna is made of enameled copper with a diameter of 0.35 mm.

Referring to FIG. 8, the antenna has the following parameters.
Maximum diameter: 7.5 mm to 9 mm
Apex-end diameter: 2 mm to 4 mm
Number of turns: turns: 7 to 10
H=2.5-4 mm (designed for 2.6 but manufactured 3.25)
Angle: 60° to 80°
Thickness of the wire: 0.2 mm to 0.5 mm
Material: enameled copper, but in other embodiments it could be silver, aluminium, stainless steel.

The antenna can be also encapsulated in a coating. The coating material may be one or more selected from be epoxy, polyurethane, parylene and benzo-cyclo-butene (BCB), polytetrafluoroethylene (PTFE), perfluoroalkoxy alkanes (PFA) and fluorinated ethylene propylene (FEP).

The antenna is placed at one end of the capsule and at a minimum of 5 mm from the batteries. Its shape is designed also to maximise the volume available within the capsule.

Figure 9:
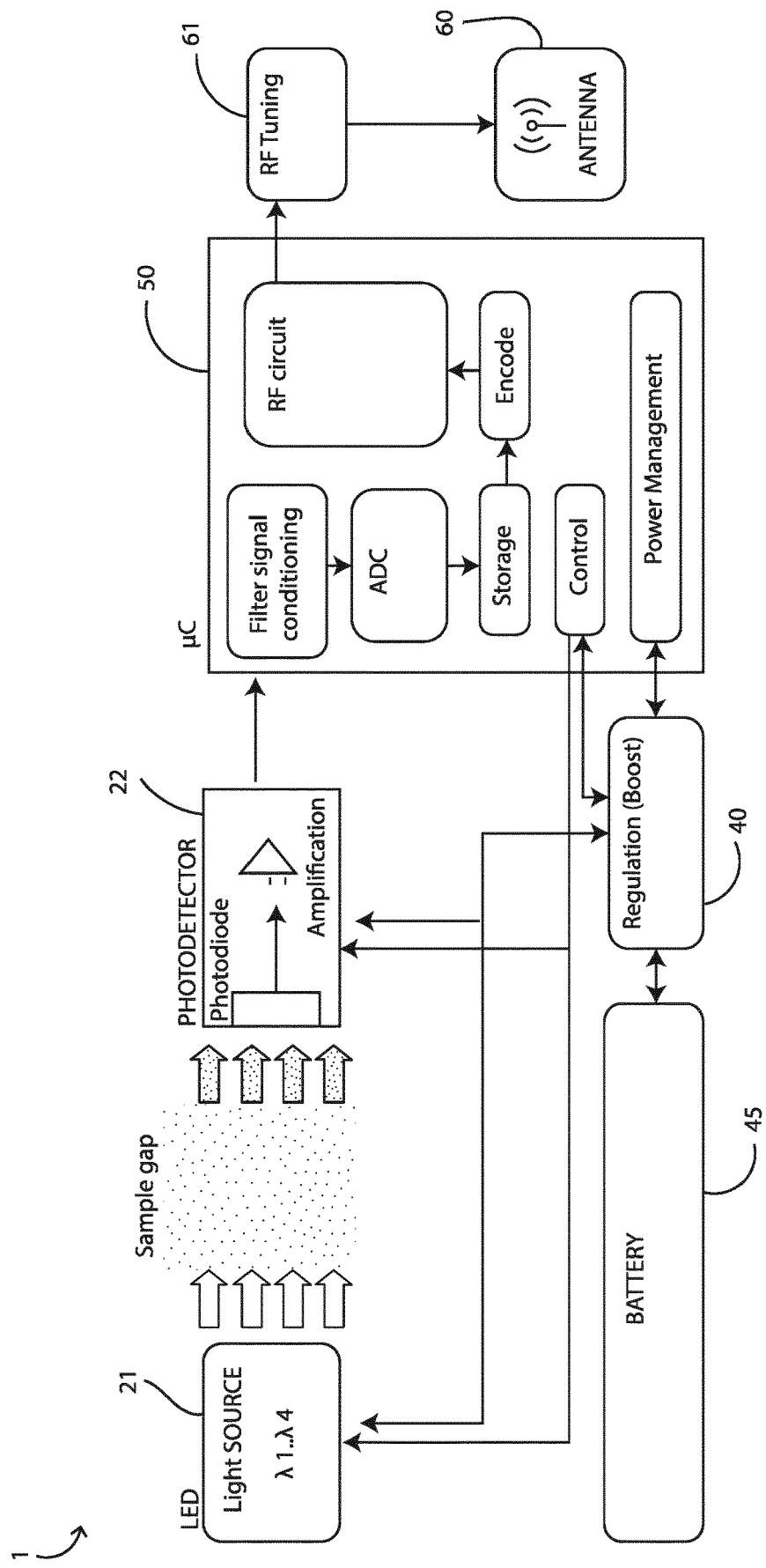
FIG. 9 is a block diagram of the sensing system.

FIG. 9 shows the architecture in logic terms. The microcontroller 50 is physically close to the antenna 60, with an RF tuning component on the board 50. The microcontroller 50 also has the following sequence of functional blocks:
filter signal conditioning, linked to the PD 21,
an ADC, in turn linked to storage, an encode function, and in turn an RF circuit,
a control block controls the regulation circuit 40, which is linked to a power management block on the chip 50.

Figure 10:
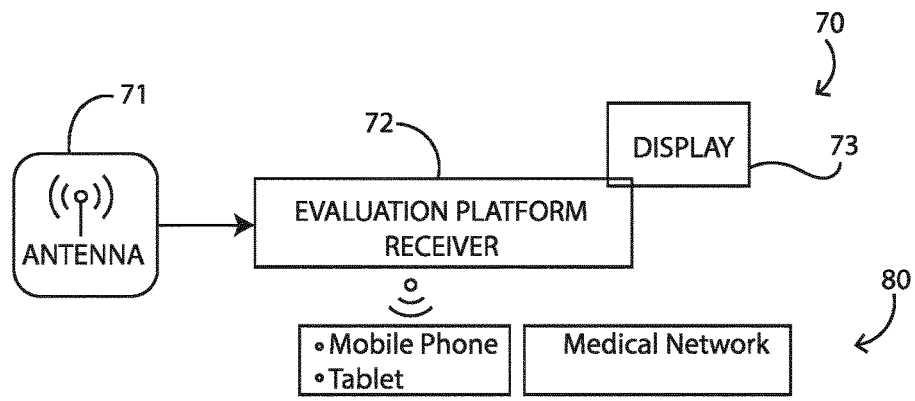
FIG. 10 is a block diagram of a receiver-side architecture of a system incorporating the sensor.

FIG. 10 shows a system incorporating the capsule 1, including a receiver 70 arranged to receive radiation signals from the capsule's antenna 60. The receiver side architecture is shown in FIG. 10 and shows the logic layout with the receiver 70 including an antenna 71, an evaluation platform receiver 72, and a display 73. There is also a local area wireless link to user devices 80.

The absorption mode uses an optical system to identify blood and using the light absorption property of the blood. Each substance has its own light absorption profile, i.e. old blood and active bleeding.

Figure 11:
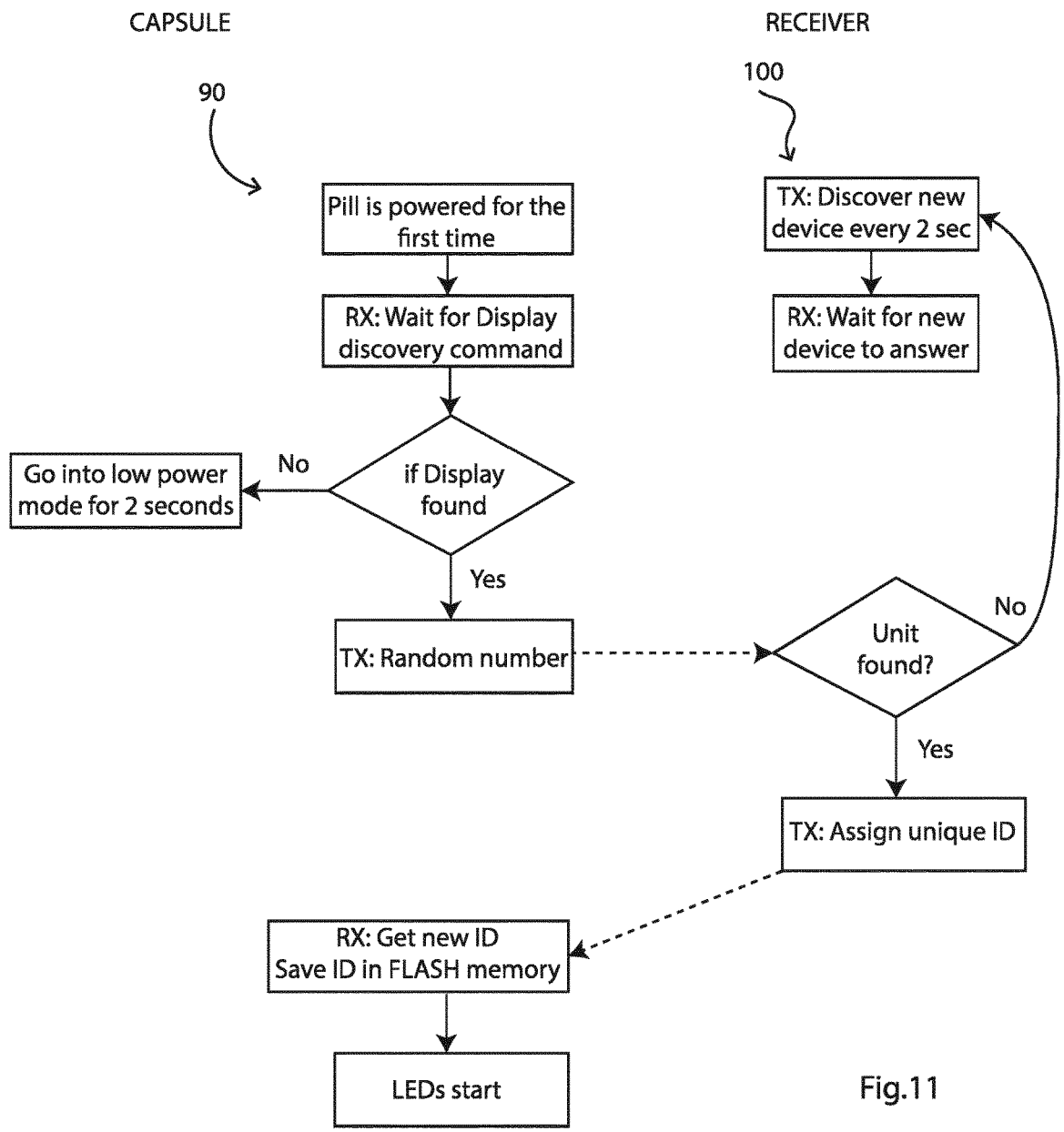
FIG. 11 is a flow chart showing an example of operation of the system.

Referring also to FIGS. 11 and 12, operation of the capsule and the system is described. The hardware components of the system are the components 20 within the capsule and the receiver components 70.

The capsule is ingested and travels along the GI tract without the need of any external intervention. The capsule can also incorporate a location sensor (e.g. based on pH, GPS, etc.) to inform on its position along the journey. If monitoring over a longer period of time is required, the capsule can be placed in a specific location of the GI tract with a minimally invasive procedure. The capsule is configured to have a through hole feature 11 at one end (see FIG. 2) so that a string/suture can be secured to the capsule. The string/suture can be biodegradable to ensure a double release mechanism. The suture passage 11 is streamlined, not affecting the overall envelope of the capsule, and may be used if needed at the choice of the physician according to the medical circumstances. This allows excellent versatility.

The light source 21 emits light at different wavelengths within the visible spectrum, including a violet light, a blue light, a green light, a yellow light, an orange light and a red light. Each substance of blood has its own light absorption profile and the wavelengths are selected to amplify irregular characteristics of the blood absorption spectrum. The photodetector 22 covers the whole visible spectrum, detecting the light and transmitting it to the amplifier, which collects and transforms photons into voltage/current and then converts it into a digital signal.

The light source can comprise a singular light source or an array of multiple light sources, similarly the photodetector can be a singular photodetector or an array of multiple. In one example, a single light source 21 emits light at any of four wavelengths within the range 300 nm to 900 nm, and the photodetector 22 configured to cover said whole spectrum, from 300 nm to 900 nm.

Figure 12A:
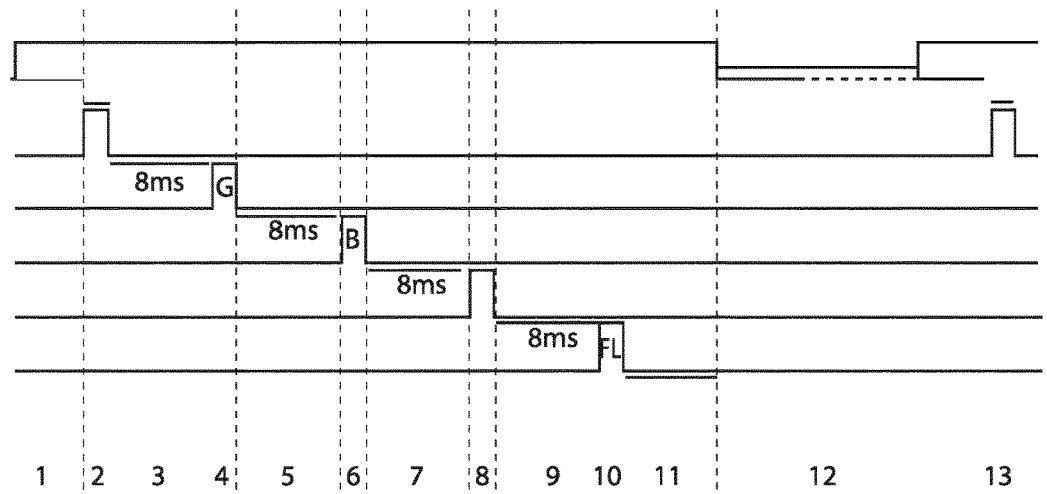
FIG. 12(a) is diagram of an LED drive scheme with time multiplexing.

FIG. 11 shows an example of a control strategy, and FIG. 12(a) shows an LED light emitter driving pattern. The microcontroller 50 activates the LEDs to enhance optical performance while limiting power consumption. The evaluation platform 72 is programmed with a decision-making model and is configured to predict the probability that the analysed medium is blood.

The microcontroller can be configured to pulse the LEDs sequentially, for emission at its particular wavelength, and short pulses are preferable to optimise battery. It will be appreciated that some or all of the components can be integrated, such as the photodetector, amplification, microcontroller and RF module.

As shown in FIG. 12(a), the individual wavelengths are activated with a time delay of 8 ms in-between, hence operating a form of time-division multiplexing on the channel between the walls 6 and 7. This channel is through the volume within the cut-out defined by the walls 5, 6, and 7.

In one embodiment the following is a sequence for operation of the capsule.

The microcontroller enables LED1 (=LED1 is on).
The microcontroller also enables the photo-detector 22 and takes 10-30 measurements from the photo-detector 22. The photo-detector 22 sends the 10 to 30 voltage signals to the ADC of the microcontroller. The microcontroller is programmed to eliminate the higher and the lower values and it averages the remaining values. This resulting number VLED1 is a voltage which is proportional to the absorbed light received by the photo-detector while LED1 is on.
LED1 is switched off after about 2 ms to 5 ms.
LED2 is now turned on.
The photo-detector 22 measures the VLED2.
LED2 is tuned off after 2 to 5 ms.

This sequence is repeated for each LED. When all of the LEDs have been pulsed and all of the VLEDn (voltage levels of signals for the relevant wavelength of emission) have been recorded, all LEDs are switched off and the photo-detector takes the latest set of measurements when no light sources are active. The VLED_OFF is a sign of possible ambient or environment light and it is then used to eliminate possible light background noise.

At this point, the photo-detector is also switched off until a new set of measurements have to be made.

The frequency of measurements is programmed based on the clinical conditions. A slow frequency (e.g. every 1-2 minutes) is implemented when the results show that the risk of bleeding is low. As soon as the system detects the possibility of a bleed, the frequency can be automatically updated to ensure a better monitoring (e.g. every 2 seconds).

The data can be used to detect the presence of blood in a manner which is instantaneous. For example:

if LED1=RED light (620-700 nm), LED2=Far_Red (700-750 nm); LED3=Green light (495-570) and LED4=Blue light (450-495), we have the following conditions to estimate the presence of blood:

If $V_{RED}/V_{GREEN} = R_1 >$ threshold1 → BLOOD

OR if $V_{FAR\_RED}/V_{GREEN} = R_2 >$ threshold2 → BLOOD

OR if $V_{RED}/V_{BLUE} = R_3 >$ threshold3 → BLOOD

OR if $V_{FAR\_RED}/V_{BLUE} = R_4 >$ threshold4 → BLOOD

OR If $V_{FAR\_RED}/V_{RED} = R_5 >$ threshold5 → BLOOD

OR $V_{RED}$ & $V_{GREEN}$ & $V_{BLUE} <$ threshold6 → BLOOD

OR $V_{RED}$ & $V_{FAR\_RED}$ & $V_{GREEN}$ & $V_{BLUE} <$ threshold7 → BLOOD

OR $\arctan(\lambda_{GREEN} - \lambda_{BLUE})/(V_{GREEN} - V_{BLUE}) = \Theta_1 > \Theta_{THRESHOLD\ 1}$ → blood OR $\arctan(\lambda_{RED} - \lambda_{GREEN})/(V_{RED} - V_{GREEN}) = \Theta_2 > \Theta_{THRESHOLD\ 2}$ → blood OR $\arctan(\lambda_{FAR\_RED} - \lambda_{RED})/(V_{FAR\_RED} - V_{RED}) = \Theta_3 > \Theta_{THRESHOLD\ 3}$ → blood Where all of the threshold values are values within an arbitrary unit range such as 1.8 to 2.2; threshold values are values within the range 0 to 300 mV, and $\Theta_{THRESHOLD\ 1}$, $\Theta_{THRESHOLD\ 2}$, $\Theta_{THRESHOLD\ 3}$ are angles within the range 0° to 70°.

Figure 12B:
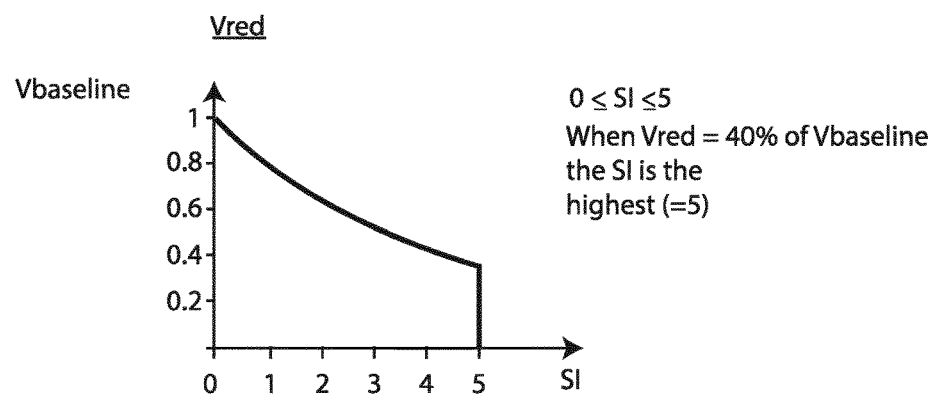
FIG. 12(b) is a plot of a voltage parameter vs. severity index ("SI") for sensing by the capsule.

In the above, $\lambda_{GREEN}$, $\lambda_{BLUE}$, $\lambda_{RED}$, $\lambda_{FAR\_RED}$ are the wavelengths for these colours, for example for green it is preferably between 560-520 nm, If blood has been detected using one or multiple conditions stated above, it is possible to identify a severity index (SI) of the bleed. The severity index (SI) is calculated as the percentage drop of $V_{RED}$ and/or $V_{GREEN}$ at a certain time compared to base initial values of $V_{RED}$ and/or $V_{GREEN}$ when there is no blood. At higher concentrations of blood, the absorption of red and/or green light is higher and therefore the voltage measured by the photo-detector 22 decreases, as shown in FIG. 12(b).

Figure 12C:
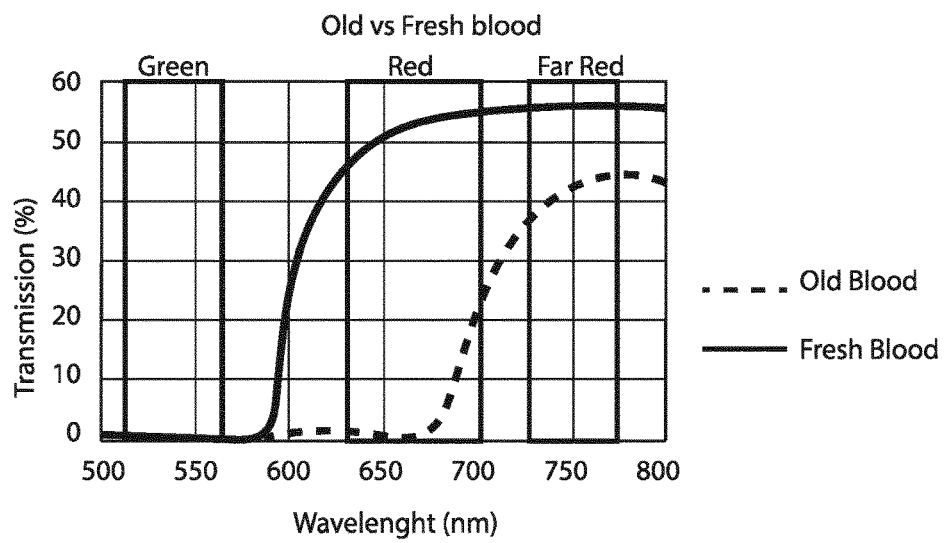
FIG. 12(c) is a plot showing differences in transmission characteristics between old blood and fresh blood and how this is used for SI calculation.

Also, FIG. 12(c) shows how the processor can distinguish fresh vs. old blood. The system can use different light to detect new blood (vivid red blood colour) from the old blood (which has a brown component due to oxidation of haemoglobin). For example, the processor can use FR/R for old blood and FR/G for fresh blood. As shown in FIG. 12(c) there are significant differences in the values.

By using at least four wavelengths more accurate information is provided, akin to a discrete spectrophotometer. Blood at high concentration also absorbs the Red light, so the presence of blood cannot depend uniquely from the ratio but absolute values must also be considered. Also, by considering the absolute values of some wavelengths (for example the green light absorption), the algorithm can correlate to the blood concentration.

In another embodiment, each light source has a specific wavelength and also a specific optical power that can be regulated by the microcontroller. The microcontroller can increase or decrease the activation time of each LED resulting in a chosen light intensity.

Figure 12D:
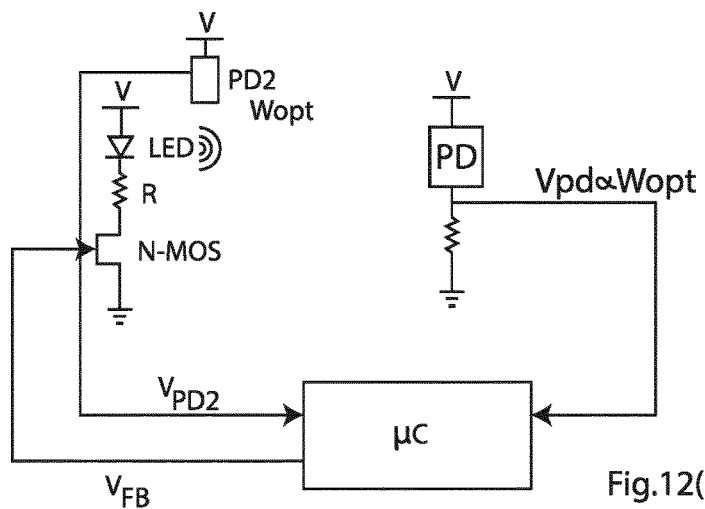
FIG. 12(d) is a circuit diagram of an arrangement for sensing of emitted light and providing feedback.

In alternative, resistors may be used to regulate the output light intensity. Referring to FIG. 12(d) the circuit may be configured with components such as N-MOSFET to act as a voltage controlled resistor. In this case, an optical sensor photo-diode PD2 is provided to feed the information back to the microcontroller µC in order to continuously adjust the output. For example, there may be one target for a stationary capsule, and a different one for travel through the GI tract.

Using any of these mechanisms the microcontroller can implement a specific intensity for each LED in order to control the required optical power output.

It will be appreciated that the processor provides full results by instantaneous measurements as described above, based on combinations of wavelengths.

As described above, the Severity index (SI) is determined as the percentage drop of one single light wavelength from the expected "no blood condition" light wavelength.

It is also advantageous that the capsule can be placed in a single position for a particular period of time, as noted above.

ALTERNATIVE EMBODIMENTS

Figure 13A:
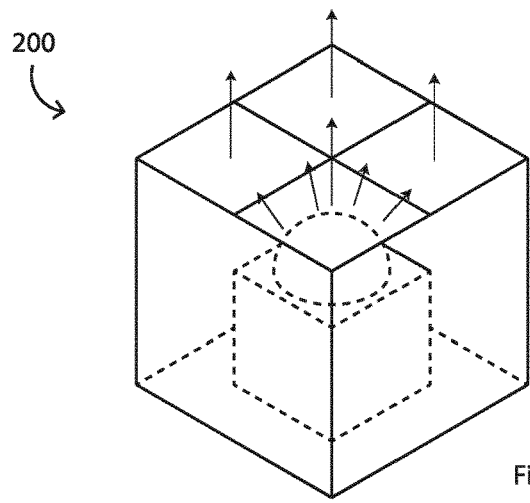
FIGS. 13(a) and 13(b) are diagrams illustrating alternative light source arrangements.
Figure 13B:
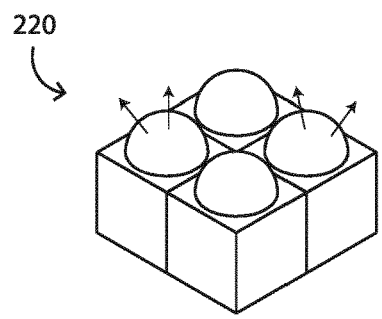
Figure 14A:
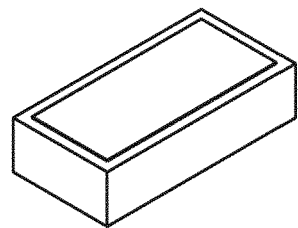
FIGS. 14(a) to 14(d) are diagrams showing various detector arrangements.
Figure 14B:
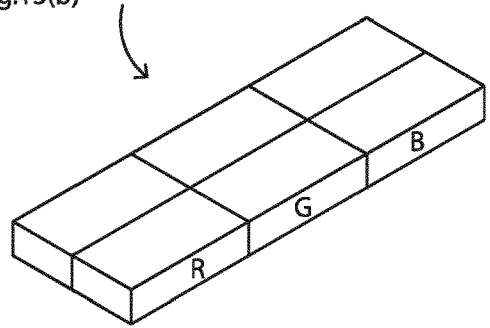
Figure 14C:
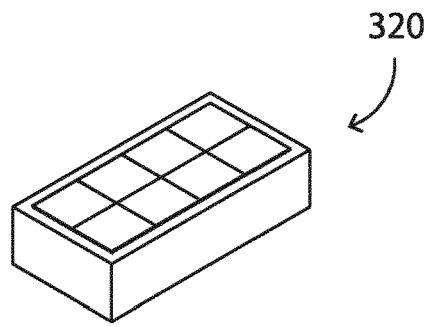
Figure 14D:
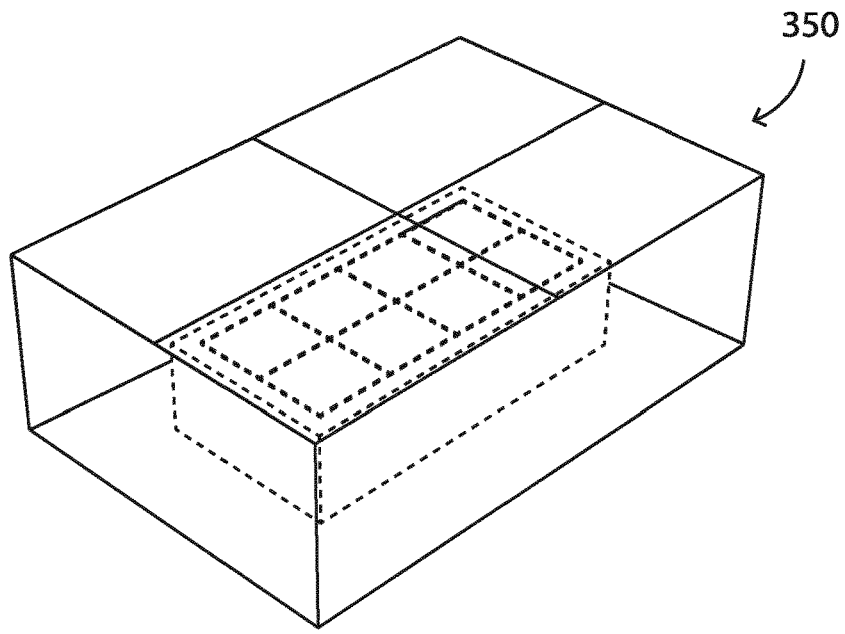

FIG. 13 shows different arrangements of light sources that could be used in alternative embodiments. One or multiple discrete light emitting diodes (LEDs) provide the desired wavelengths. There may be a source 200 with a single broadband LED and multiple filtering lenses each providing an associated wavelength, in this example G, B, R, and Far Red (FIG. 13(a)). As shown in FIG. 13(b) there may be an array 220 of discrete LEDs each providing a specific wavelength.

FIG. 14 shows various options for the photo-detector as follows:
(a) Broadband photo-detector 300,
(b) Multiple discrete photo-detectors 310,
(c) One component 320 with multiple sensitive areas, each sensitive to a specific wavelength,
(d) An assembly 350 of a broadband PD with a detachable cover to filter selectively.

Light sources, photo-detectors and optical components (for example filters, collimators and fibre optics) are assembled in order to ensure both absorbance and fluorescence detection. The distance and angle of the components in relation to each other is selected to ensure performance of sensors while minimizing volume and weight of components.

Figure 15:
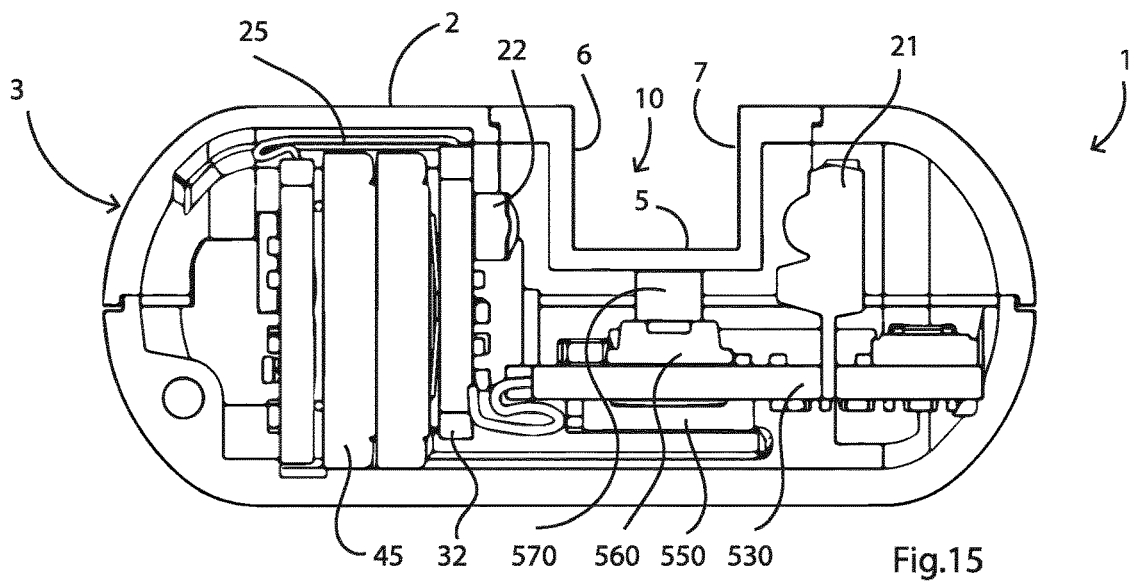
FIG. 15 is a sectional side view of an alternative sensor, in this case with a fluorescence detector.
Figure 16:
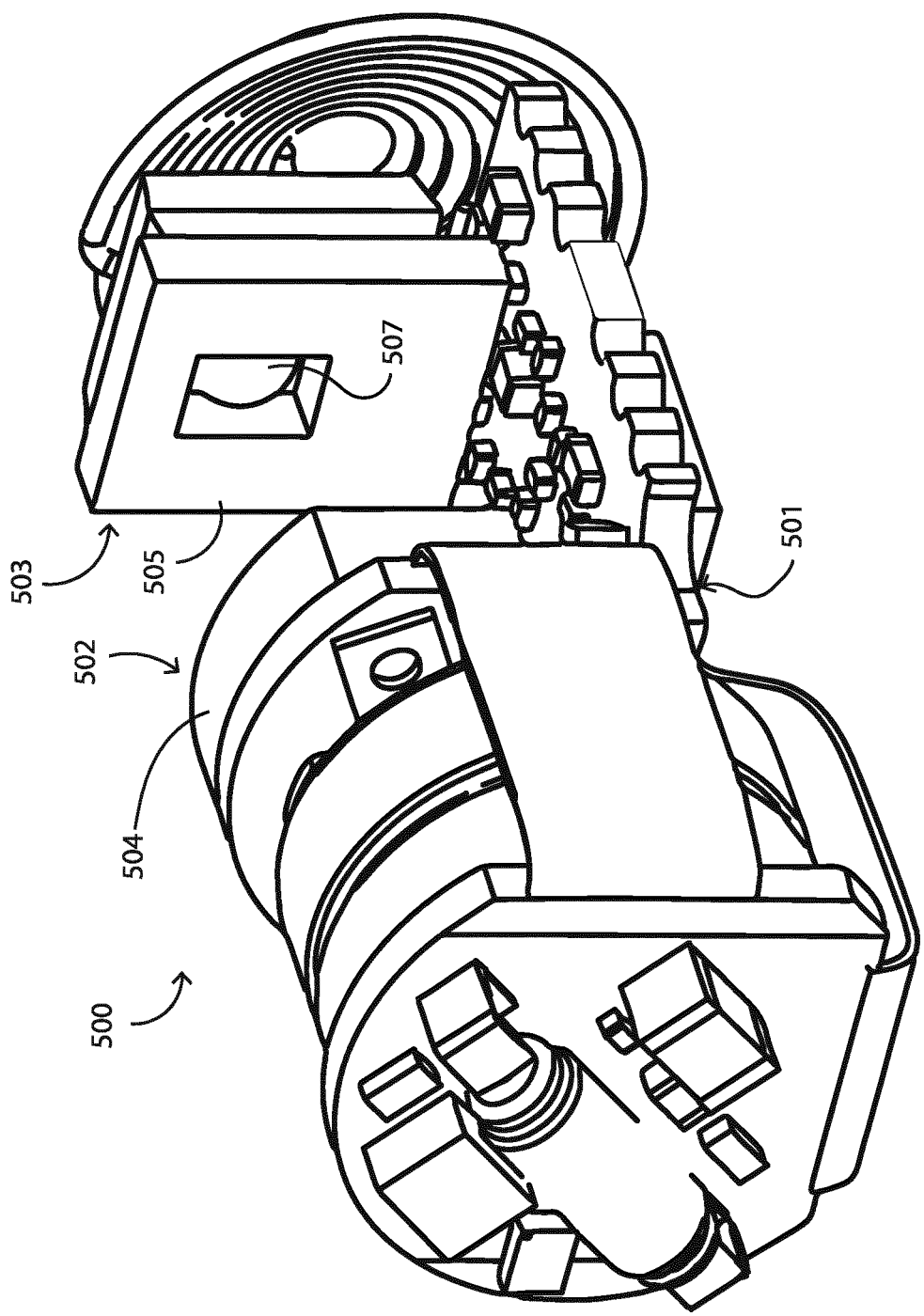
FIGS. 16 and 17 are perspective views from opposed ends of the internal assembly of an alternative sensor.
Figure 17:
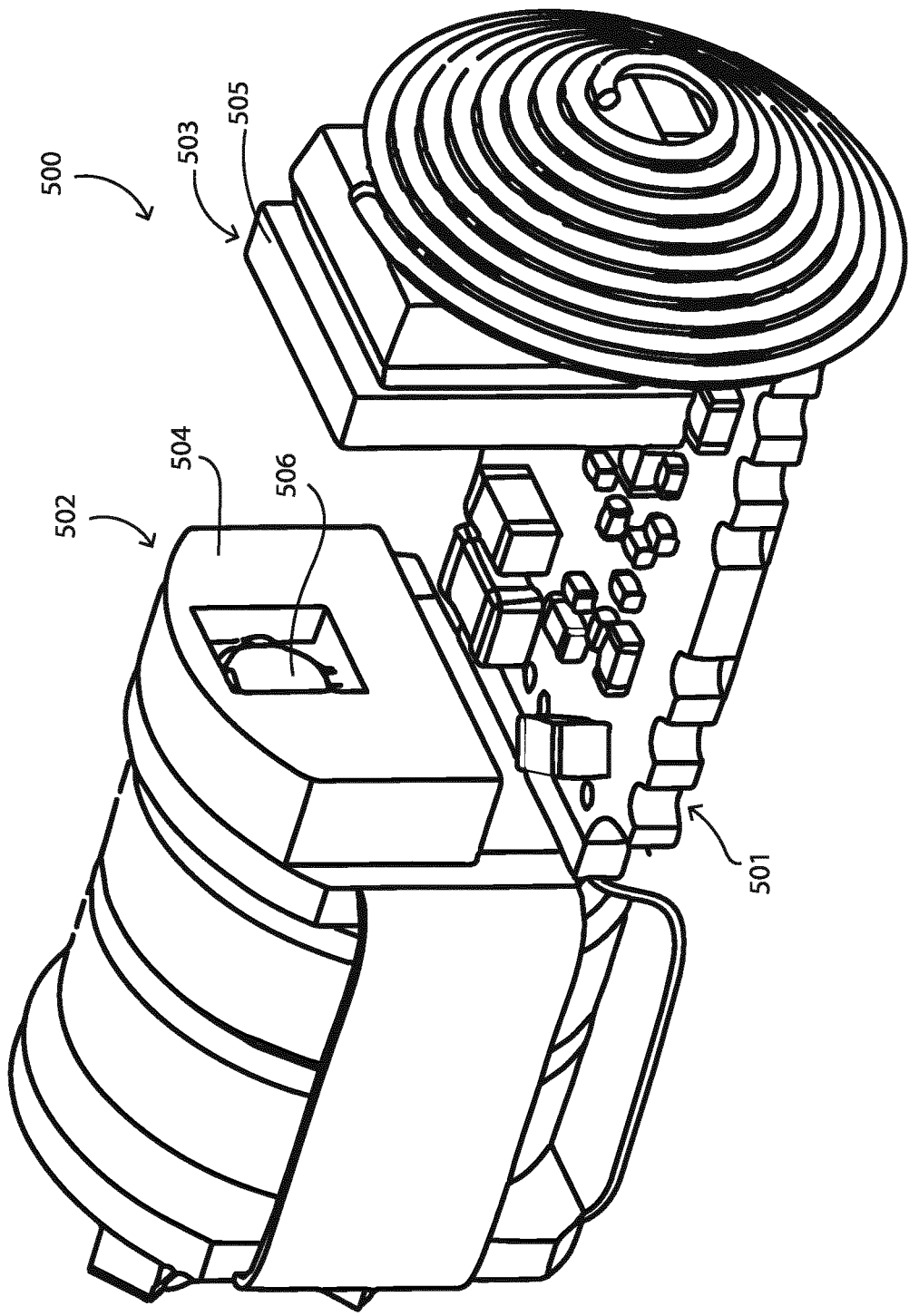

Referring to FIG. 15 an alternative sensor capsule has some similar components, indicated by the same reference numerals. In this case there is a fluorescence detector 560 under a filter 570 in contact with the base wall 5, which is transparent to light. Illumination to cause fluorescence is caused by operation of the emitter 22, causing fluorescence within the cut-out volume during a time slot for emission of the relevant wavelength.

The walls 6 and 7 ensure that the light source and the detector are facing each other for absorption-based measurements. The wall 5 is placed at 90° to the wall 6 for fluorescence measurements. This will minimise the crosstalk between the fluorescence light source and the detector. This solution, together with optical filters and collimators will ensure good fluorescence measurements performance even in a miniaturised environment. Optical filters and collimator can be incorporated in the lens 3.

In the case where the fluorescein mode is operated in the capsule, fluorescein is required to be intravenously injected, to be pumped across the body and if the patient has an active upper gastrointestinal bleed, part of the fluorescein will leak inside the stomach together with the blood.

In the case of fluorescein, the fluorescein reaches the stomach if internal bleeding is occurring, thus the system can identify active bleeding.

Figure 18:
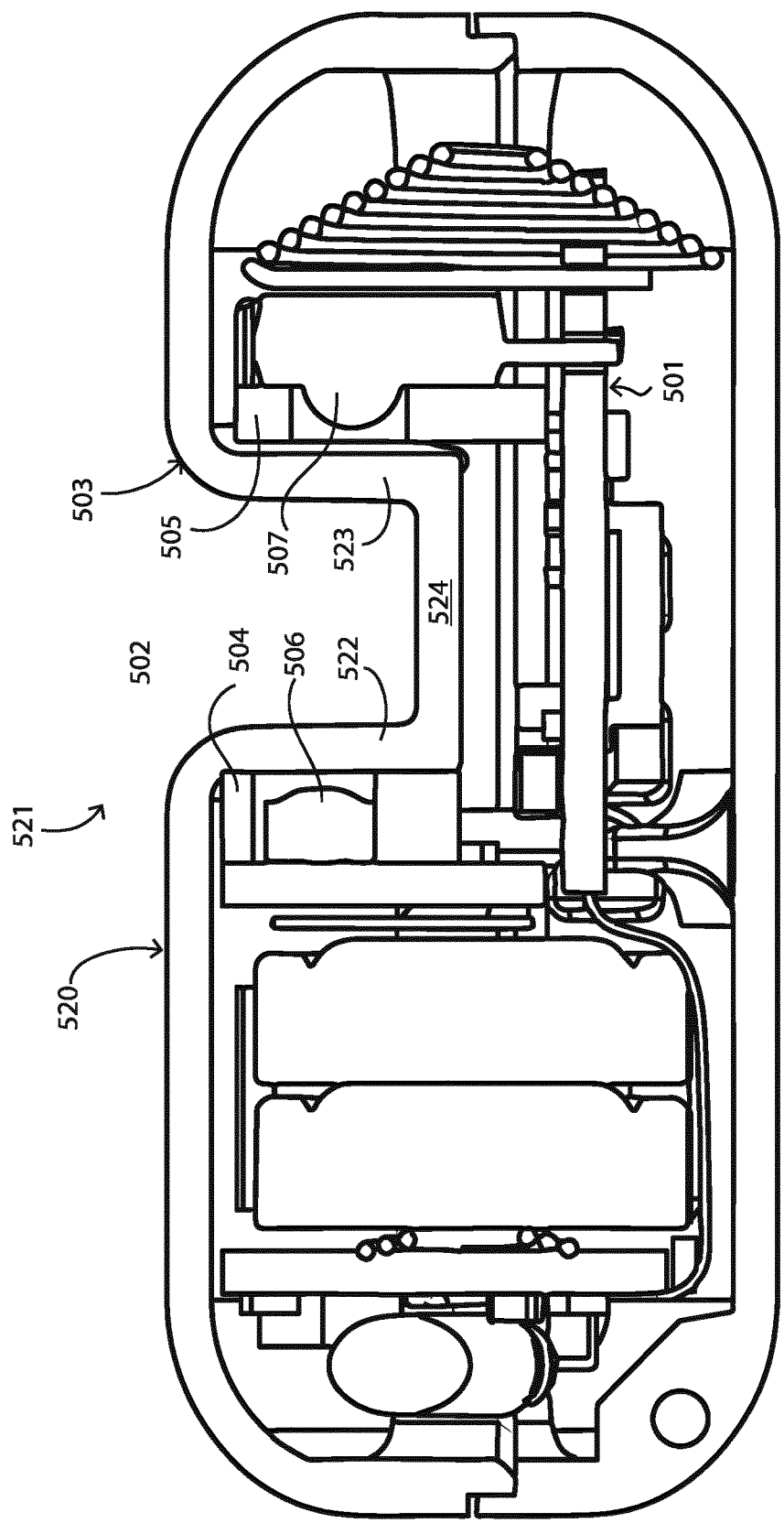
FIG. 18 is a diagrammatic sectional view through the sensor of FIGS. 16 and 17.
Figure 19:
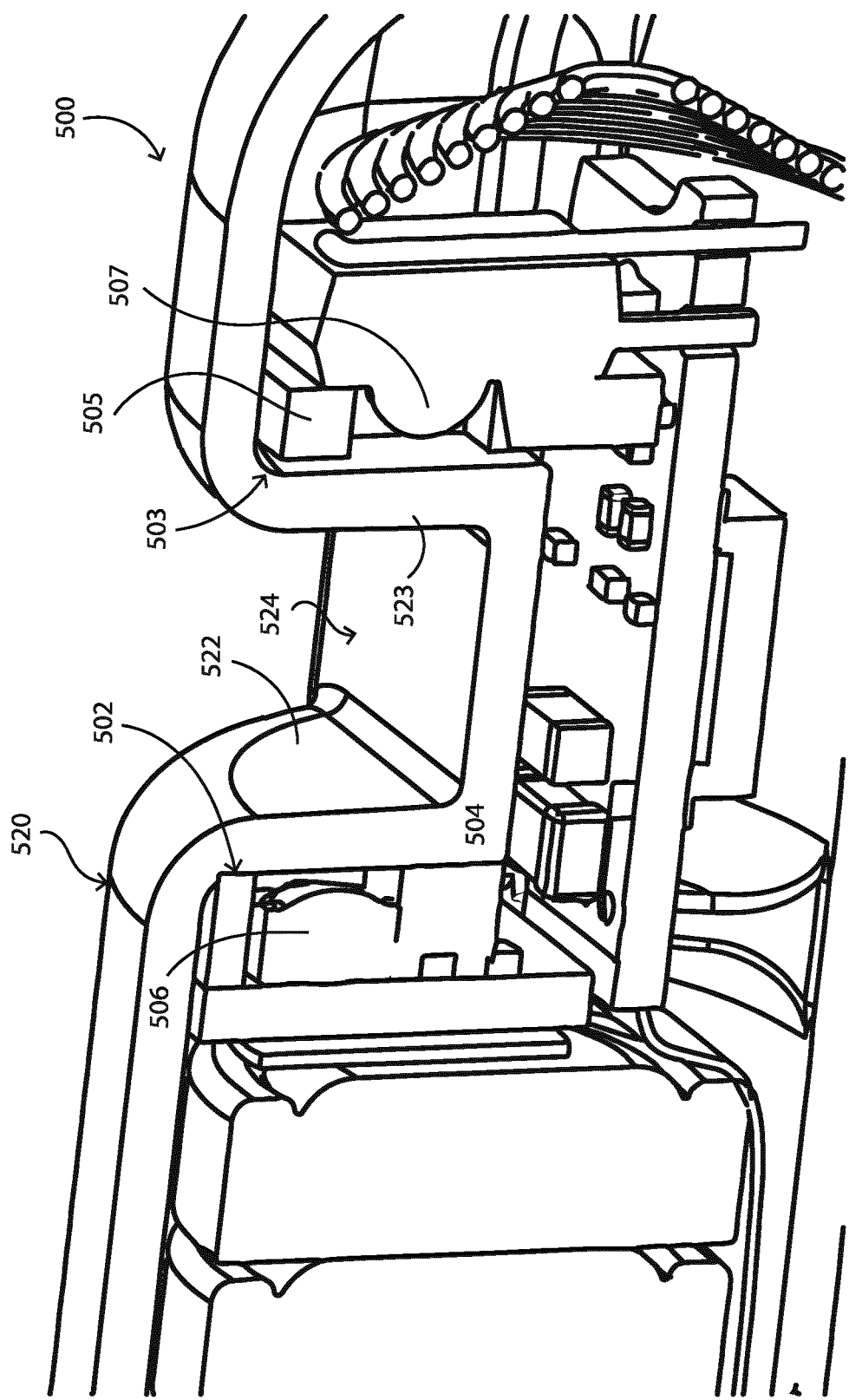
FIG. 19 is a cut away perspective view of the sensor of FIGS. 16 to 17.

Referring to FIGS. 16 to 19 there is illustrated a capsule 500 with a light source 502 and a light detector 503 having black light-absorbing shields (black plastics material) 504 and 505 respectively surrounding a path from a light emitter 506 to the housing wall, and a path to a detector 507 on the opposed side of the gap (external space for analysis). FIGS. 18 and 19 show how the light source 502 and the light detector 503 are mounted on a substrate 501, and the relative positions of these components relative to the housing 520.

FIGS. 18 and 19 show the relationship of the light source and detector to the housing, showing the housing 520 having a wall 522 near the source 502 and a wall 523 near the detector 503. Also, there is a base wall 524 of the external detection space. Each light absorber 504 and 505 forms a light channel surrounded on four sides by light-absorbing material such as black plastics material or alternatively channeled within a fibre optic tube.

Advantageously, the light absorbers absorb light which is not close to the optical axis between the source and the detector. This helps to prevent radiation from scattering within the capsule and reaching the detector 507 as noise. The prevention of noise can be aided also by a light shield adjacent the housing wall at the base of the gap.

This arrangement very effectively channels the light from the emitter into the photodetector, for both absorption and fluorescence modes of operation. For fluorescence, the light of the source reaches the sample medium to excite the fluorescence material and only the emitted light reaches the photodetector, the light coming from the source being noise.

Either or both of the light absorbers can be provided by a component attached to the light emitter device, or can be part of light emitter device packaging, or can be part of the housing.

There may be at least one LED that emits the light within the excitation wavelength of the Fluorescein sodium, for example approximately 490 nm. The photodetector 560 comprises one optical filter to filter out all the unwanted wavelengths excepting the light emitted from the excited Fluorescein sodium, for example approximately 520 nm. The light is converted into voltage by a light-to-voltage converter in a similar way as before. Blood that leaks into the stomach brings with it fluorescein, and the light produced by the excited fluorescein is proportional to the amount of fluorescein. Hence, the existence and severity of an internal bleed is detected. Fluorescein is rapidly metabolised and it will become ineffective after 20-30 minutes and will no longer emit measurable fluorescence. This is a very effective mechanism to instantaneously detect active bleeding in real time. In some uses this mechanism may be in addition to or instead of the light detection methods described above. When the capsule is used it may be user-configured to use one or both mechanisms.

The capsule can have one or multiple sampling areas where the blood or other fluids can flow. For example, by having two cut-out volumes at the two extremities of the capsule on opposed sides with respect to a longitudinal axis, the capsule can sample the environment regardless of the capsule orientation.

The capsule may have in other embodiments a hydrophilic material coating, or a PH sensitive coating with a light sensor to assess the status of the coating; this can be used to locate the capsule within the GI tract or as PH monitor.

Components of the capsules of various embodiments may be combined in different manners to suit the circumstances. For example, different combinations of LED wavelengths may be used. The radiation wavelengths may be different from those described, potentially further outside the visible spectrum. Also, it is not essential that the antenna is all or partly within the housing. It is envisaged that it may be at least partly externally mounted, and some of it may be embedded within the housing material. The radiation emitter drive circuit and the signal processing circuit linked to the detector may have any desired level of data processing capabilities, ranging from the basic for driving the emitter and receiving signals from the detector to more comprehensive processing. Where the level is basic more processing would be performed on the external device with which the capsule communicates. On the other hand, the system may comprise only the capsule, with the signal processing circuit being configured to transmit full-processed signals for reception by an external computing device.

The invention is not limited to the embodiments described but may be varied in construction and detail. For example, instead of having LEDs and PDs on opposed sides of the gap, they may be located on the board, and optic fibres may be arranged to direct light to where the LEDs are and to receive light from where the PDs are. This would have the benefit of the active electronic components all being mounted on the one substrate.

The invention claimed is:

1. A biosensor system comprising:
a capsule comprising:
  a housing configured for ingesting in a mammal GI tract and having a longitudinal axis, at least some portions of the housing being transparent to radiation of a sensing wavelength, and wherein the housing is configured to form an external space which is open to access by fluids,
  a radiation emitter and a radiation detector arranged to emit radiation into said external space and to detect radiation from said external space, through said transparent portions of the housing,
  a drive circuit for the radiation emitter and a signal processing circuit linked to the detector, and
  an interface with an antenna for wireless transmission of data to a processor for locally processing and storing detection data,
  wherein the emitter comprises a plurality of emitter devices each adapted to emit at a particular wavelength and the drive circuit is configured to activate each emitter device according to a time multiplex scheme,
  the signal processing circuit being configured to determine a ratio of far red/red to indicate old blood and a ratio of far red/green for fresh blood.

2. The biosensor system as claimed in claim 1, wherein the housing forms a convex lens for passage of radiation from the emitter into the external space, and a concave lens for passage of radiation into the detector.

3. The biosensor system as claimed in claim 1, wherein the signal processing circuit comprises a processor mounted on a controller circuit board which extends in a longitudinal direction and overlaps with said external space, and the wireless interface includes an antenna which is mounted in a domed end of the housing.

4. The biosensor system as claimed in claim 1, wherein the antenna is in the form of a spiral with decreasing diameter in a direction towards an end of the housing; and optionally the antenna has a maximum radial dimension in the range of 7.5 mm to 9 mm and it narrows to form an apex with a radial dimension in the range of 2 mm to 4 mm.

5. The biosensor system as claimed in claim 1, wherein the number of turns of the antenna is in the range of 7 to 10, and the antenna shape outer envelope substantially forms an angle to the longitudinal axis in the range of 60° to 80°.

6. The biosensor system as claimed in claim 1, wherein the wireless interface comprises RF circuits located physically adjacent the antenna, on a board extending longitudinally, and optionally the signal processing circuit comprises a processor mounted on a circuit board extending longitudinally.

7. The biosensor system as claimed in claim 1, wherein the time separation between emitter device activations is in the range of 2 ms to 5 ms.

8. The biosensor system as claimed in claim 1, wherein there is a particular ratio threshold for each of a plurality of combinations of radiation wavelengths.

9. The biosensor system as claimed in claim 1, further comprising determining ratios of one or more of: red:green, red:blue, far red:blue.

10. The biosensor system as claimed in claim 1, wherein the signal processing circuit is configured to determine an indication of presence of a particular fluid according to determining an angle as an arctan of a wavelength difference divided by a difference in detected signal, and comparing said determined angle with a threshold angle.

11. The biosensor system as claimed in claim 1, wherein the signal processing circuit is configured to determine a severity value for an indication of presence of a particular fluid according to detected signal amplitude for one or more radiation wavelengths, and optionally said severity value is an indicator of extent of internal bleeding.

12. The biosensor system as claimed in claim 1, wherein the signal processing circuit is configured to determine a proportion of fall in detected signal strength for one or more emitter wavelengths as a parameter in determining the severity value, and wherein the signal processing circuit is configured to set an intensity for the light source, and wherein the signal processing circuit is configured to set an intensity at a particular time, such as by limiting light emitter drive current, and wherein the signal processing circuit is configured to control average light emission intensity over a period of time by controlling length of ON durations, and wherein the signal processing circuit comprises a light sensor and the processor is configured to process feedback signals from said sensor to adjust light emitter output.

13. The biosensor system as claimed in claim 1, including a light-absorbing guide surrounding a path between the radiation emitter and/or detector and the housing wall, and optionally the guide comprises a substantially black material, and optionally said guide comprises an optic fibre.

* * * * *